United States Patent
Malagnino

(10) Patent No.: US 9,408,674 B2
(45) Date of Patent: Aug. 9, 2016

(54) REAMER WITH AN IMPROVED BLADE FOR ROOT CANAL PREPARATION

(75) Inventor: Vito Antonio Malagnino, Rome (IT)

(73) Assignee: SWEDEN & MARTINA SPA, Due Carrare (PD) (IT)

( * ) Notice: Subject to any disclaimer, the term of this patent is extended or adjusted under 35 U.S.C. 154(b) by 107 days.

(21) Appl. No.: 14/369,606

(22) PCT Filed: Jan. 30, 2012

(86) PCT No.: PCT/IB2012/050404
§ 371 (c)(1),
(2), (4) Date: Jul. 28, 2014

(87) PCT Pub. No.: WO2013/114154
PCT Pub. Date: Aug. 8, 2013

(65) Prior Publication Data
US 2014/0356809 A1    Dec. 4, 2014

(51) Int. Cl.
A61C 5/02    (2006.01)

(52) U.S. Cl.
CPC ..................... *A61C 5/023* (2013.01)

(58) Field of Classification Search
CPC ........... A61C 5/02; A61C 5/023; A61C 5/025
USPC ............................................. 433/81, 102, 224
See application file for complete search history.

(56) References Cited

U.S. PATENT DOCUMENTS

| | | | | |
|---|---|---|---|---|
| 1,022,838 A | * | 4/1912 | Funk | A61C 5/023 433/102 |
| 2,436,325 A | * | 2/1948 | Penny | B23D 43/02 407/115 |
| 4,738,616 A | * | 4/1988 | Reynaud | A61C 13/30 433/165 |
| 4,904,185 A | * | 2/1990 | McSpadden | A61C 5/023 433/102 |
| 4,990,088 A | * | 2/1991 | Weissman | A61C 13/30 433/102 |
| 5,066,230 A | * | 11/1991 | Weissman | A61C 13/30 433/102 |
| 5,735,689 A | * | 4/1998 | McSpadden | A61C 5/023 433/102 |
| 5,735,690 A | * | 4/1998 | Malentacca | A61C 3/02 433/102 |
| 5,947,730 A | * | 9/1999 | Kaldestad | A61C 5/023 433/102 |
| 6,074,209 A | * | 6/2000 | Johnson | A61C 5/025 433/102 |
| 6,261,099 B1 | * | 7/2001 | Senia | A61C 5/04 433/224 |
| 6,293,794 B1 | * | 9/2001 | McSpadden | A61C 5/023 433/102 |
| 6,579,092 B1 | * | 6/2003 | Senia | A61C 5/023 433/102 |
| 2006/0210947 A1 | * | 9/2006 | Lampert | A61C 5/023 433/102 |
| 2007/0037117 A1 | * | 2/2007 | Jaunberzins | A61C 5/023 433/102 |
| 2010/0119990 A1 | * | 5/2010 | Lampert | A61C 5/023 433/102 |

FOREIGN PATENT DOCUMENTS

| | | |
|---|---|---|
| EP | 1829498 | 9/2007 |
| WO | WO2010086887 | 8/2010 |

* cited by examiner

*Primary Examiner* — Nicholas Lucchesi
(74) *Attorney, Agent, or Firm* — Themis Law

(57) ABSTRACT

A reamer for use in root canal preparation includes a blade that is spiral-shaped with a pitch increasing towards the tip, and with a cutting or non-cutting tip. At given points along the length of the spiral of the blade, there is a plurality of gaps, the spiral starting again beyond the gaps, wherein the portion where the spiral is interrupted has either a constant or decreasing cross section linking the two diameters before and after the gap.

7 Claims, 1 Drawing Sheet

REAMER WITH AN IMPROVED BLADE FOR ROOT CANAL PREPARATION

FIELD OF THE INVENTION

The present invention relates to a reamer with an improved blade for Ni—Ti instruments used in root canal preparation.

More in particular, the invention concerns an instrument of the above-mentioned type with a dual-profile blade and with characteristics that facilitate the use of the instrument by the dentist.

BACKGROUND OF THE INVENTION

It is common knowledge that the use of nickel-titanium instruments in root canal preparation has become widespread in recent years.

These instruments are used inside the root canal and operated with a continuous rotary movement induced by a "counter-angle" handpiece connected to a dental endo motor that enables a speed of rotation in the range of 250 to 350 revolutions per minute.

A continuous rotation at this speed enables great efficiency and excellent working rates to be achieved.

This speed of rotation can be used with Ni—Ti instruments, not with conventional steel instruments, because the Ni—Ti alloy has a characteristic superelasticity, and consequently assures the flexibility and elasticity (or shape memory) needed to enable the rotating instrument to advance through the root canal, circumferentially cutting the dentine without being deformed, even in the case of having to follow curved trajectories.

The continuous rotational movement of a spiral-shaped blade inside a canal gives rise to a spontaneous forward displacement of the instrument, in much the same way as a screw being turned inside a suitable medium.

This tendency of the instrument to advance as it rotates gives rise to the need for the dentist to "control" this forward displacement in order to avoid an excessively rapid, "uncontrolled" progression that would carry a risk of the instrument jamming or even breaking This control is normally exerted by means of an "incremental" forward displacement, approximately 1 mm at a time, achieved manually by the dentist, i.e. the instrument is allowed to advance 1 mm and then withdrawn slightly before it is allowed to advance again, and so on.

Despite the use of this advancing technique, it nonetheless sometimes happens that the instrument suddenly accelerates out of control as it advances, engaging with an excessive length of root canal wall, and consequently becomes jammed and even risks breaking inside the root canal. This effect is known as "threading".

Since each instrument has different, precise diameters starting from the tip (every instrument has a given tip diameter and conical taper, measured in hundredths of a millimeter) and each instrument is part of a series of different-sized instruments (in particular, of increasing sizes in the case in point), the depth at which this excessive engagement may occur—and the consequent risk of "threading"—can be calculated for each of the instruments.

A first solution to this "threading" problem was proposed by company FKG and adopted in an instrument marketed by the name of RaCe®. In this case, the full length of the active, cutting edge of the blade comprises alternate 2-3 mm lengths of spiral with a given first pitch and 2-3 mm lengths of spiral with a different pitch.

In addition, there are instruments currently available on the market that are characterized by two cutting blades, an incremental pitch, and a non-cutting tip.

In particular, the latest instruments have been made with the following sequence (the first figure refers to the diameter of the instrument and the second to its taper angle): 0.10 mm—4%; 0.15 mm—5%; 0.20 mm—6%; 0.25 mm—6%. The introduction of this innovative sequence has led to the production of Ni—Ti instruments that perform distinctly better than those of the previous state of the art.

The above-mentioned solution still fails, however, to prevent any occurrence of the previously-described technical problem of "threading". A first solution to this problem has been provided by the same Applicant in the Italian patent application No. RM2009A000045 (extended as an International patent application PCT/IT/2010/00018), wherein the proposed solution involves manufacturing Ni—Ti instruments, preferably with a dual blade, with an incremental pitch and a non-cutting tip, and with a gap in the blade at a given distance from the tip designed to interrupt the advancing action of the blade and thereby prevent any "threading".

It is also well known in endodontics that increasing attention has been paid in recent years to the preparation and cleansing of the last apical millimeters of a root canal.

The dimensions of the apical foramen are often around 20-25 hundredths of a millimeter, while the millimeters of canal adjacent thereto are wider in diameter: in a horizontal cross-section, the shape is almost always an oval with its greatest diameters often exceeding 30 hundredths of a millimeter at 1 mm from the tip.

Many root canal preparation methods relying on Ni—Ti instruments involve the use of instruments that are 0.20 or 0.25 mm in diameter at the tip and with a taper angle of 4% or 6%.

When one of these instruments reaches the apex of the canal, it often leaves areas untouched in the final millimeters of the canal because the diameter of the 0.25 mm—4% and 6% instruments 1 and 2 millimeters away from the apex is narrower than the larger diameter of the canal.

One solution could consist in further increasing the conical taper of the instruments, but this would make the instrument too large in the remaining portion, so that the instrument would consequently be excessively rigid and could become more difficult to control in its forward displacement, and scarcely conservative in the coronal portion of the canal.

Another solution is the one adopted for the Protapers, which have a conical taper that is more marked in the 3 mm length nearest the tip and more limited in the remaining portion of the instrument.

SUMMARY OF THE INVENTION

The solution proposed according to the present invention is set in this context and, starting from the solution described above, as claimed in the previous patent application made by the same Applicant, it proposes to produce a Ni—Ti instrument, preferably with a dual blade, with an incremental pitch and a non-cutting tip (though a cutting tip is also feasible), and that has a plurality of gaps along the blade.

The specific object of the present invention is therefore a reamer with an improved blade for Ni—Ti instruments for use in root canal preparation, said blade having an incremental pitch and a cutting or non-cutting tip, characterized in that it has a plurality of gaps in the spiral edge of the blade at a certain distance along the length of the blade, wherein the spiral continues beyond the gap.

According to the invention, there is preferably a dual blade, said gaps being provided along the spiral of both blades.

According to the invention, moreover, beyond the gap the spiral of the blade still has the same diameter as at the point where it was interrupted, or a narrower diameter compared to its diameter before the gap.

According to the invention, in the case where the spiral of the blade begins again, beyond the gap, with a narrower diameter than it had before the gap, the portion of gap in the spiral may preferably have either a constant cross-section or a decreasing cross section connecting the two diameters before and after the gap.

Again according to the invention, the cross section of the reamer at the point where the gap occurs may be round, oval or in another shape; in particular, the cross section may be exactly the same as the cross section of the active part with straight or oblique blades, but maintaining the same diameter as at the point where the blade is interrupted or a narrower diameter, instead of an increased diameter.

In a particularly preferred embodiment of the reamer according to the invention, starting from a diameter 25, there is a first gap with a diameter of 49, beyond which the diameter returns to 49, a second gap with a diameter of 73, beyond which the diameter returns to 65, a third gap with a diameter of 89, beyond which the diameter returns to 73, and a fourth gap with a diameter of 105, beyond which the diameter returns to 97.

The invention also concerns a set of instruments having any sequence of diameters and taper angles, characterized in that each instrument features the above-described plurality of gaps in the pitch of the blade(s).

BRIEF DESCRIPTION OF THE DRAWINGS

A non-limiting example of the present invention is now described in two preferred embodiments, with particular reference to the figures in the attached drawings, wherein.

DETAILED DESCRIPTION OF EMBODIMENTS OF THE INVENTION

Figures 1, 2:
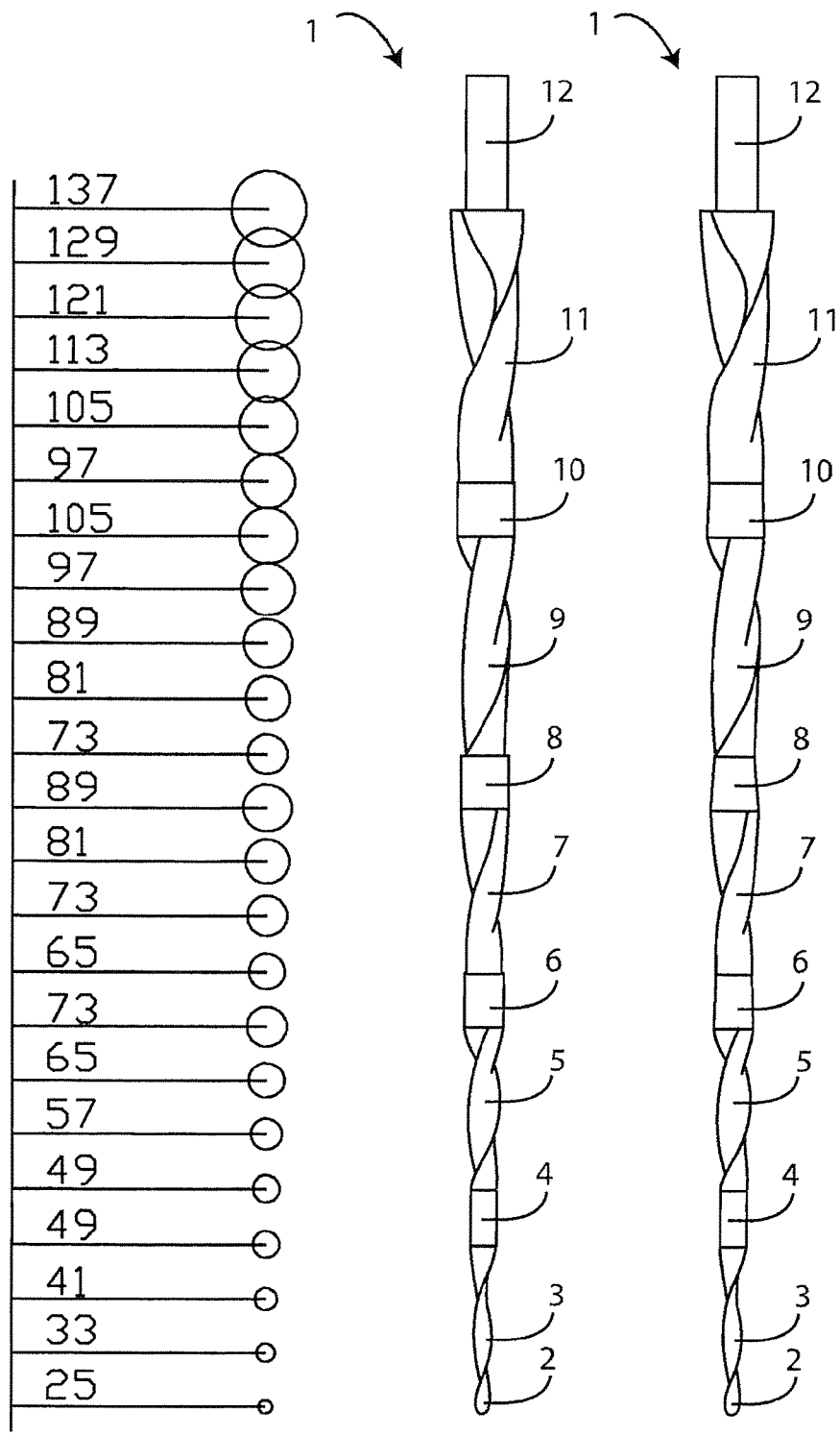
FIG. 1 is a perspective view of a first embodiment of a reamer according to the invention.
FIG. 2 is a perspective view of a second embodiment of a reamer according to the invention.

For instance, the proposed solution according to the invention may be achieved in the form of an instrument with an upper diameter of 0.20 mm or 0.25 mm at a taper angle of 6%, with a gap in the blade starting 3 mm from the tip (of a 25-8% instrument, for instance), where 1 mm of smooth portion is inserted, beyond which (i.e. 4 mm from the tip) the blade starts again with the same diameter as before the gap, or a narrower diameter, but always with the taper angle of 8%.

Another 3 mm (approximately) further on, there is again a smooth 1 mm portion, then the blade starts again (8 mm from the tip) with the same diameter as at the point where the blade was interrupted, or a narrower diameter.

This type of trend can be maintained over the full length of the active part of the instrument according to the invention.

The attached figures show two embodiments of the reamer according to the invention, generically indicated by the reference numeral 1.

Each of the reamers 1 shown in FIGS. 1 and 2 has a tip 2 (a non-cutting tip in this case, though there could also be a cutting tip without this substantially altering the solution according to the invention), with a diameter in this case of 0.25 mm.

There is a first length of double spiral increasing up to a diameter of 0.49 mm.

This is followed by a portion 4 where there is a gap in the spiral, which successively starts again with the same diameter of 0.49 mm.

After a further length of spiral 5, which increased up to a diameter of 0.73 mm, there is a further portion 6 with a gap in the spiral, which begins again with a diameter of 0.65 mm, i.e. narrower than the diameter it had before the gap.

The difference between the two embodiments shown in FIGS. 1 and 2 lies in that the portion 6 in FIG. 1 is of constant diameter, so the spiral begins again (length 7) with a step, while in the solution in FIG. 2, the portion 6 is tapered to form a link between the two different diameters.

The figures also show a further portion with a gap 8 (the spiral ending with a diameter of 0.89 mm, and starting again with a diameter of 0.73 mm), followed by a length of spiral 9, and a further gap 10 (the spiral ending with a diameter of 1.05 mm, and starting again with a diameter of 0.97 mm). Finally, there is a terminal length of spiral 11, connecting to the handpiece 12.

In the solution according to the invention, there are larger diameters in the 3 mm closest to the tip, while the diameter remains limited in size in the portion further away. The root canal is consequently not widened excessively and the instrument remains flexible. In addition, the presence of the gaps in the spiral slows the progression of the instrument and consequently enables it to be better controlled.

The present invention has been described herein as a non-limiting example, in its preferred embodiments, but this is on the understanding that changes and/or modifications may be made by a person skilled in the art without departing from the scope of the invention as defined in the attached claims.

The invention claimed is:

1. A reamer comprising:
   a Ni—Ti blade for use in root canal preparation, said blade being spiral-shaped with a pitch increasing towards a distal tip of said blade, said tip being cutting or non-cutting,
   wherein a plurality of gaps within the spiral of the blade are defined at given points along a length of the blade, interrupting the spiral, the spiral starting again beyond each gap,
   wherein each gap has a constant or decreasing cross section from a distal end of the gap, where the gap has a cross-section coinciding with the cross-section of a distally adjacent spiral portion, toward a proximal end of the gap, thereby linking two diameters of the spiral before and after the gap, and
   wherein a diameter of the spiral at the distal end of each gap is equal or larger than the diameter of the spiral at the proximal end of the same gap.

2. The reamer according to claim 1, wherein the reamer has a double spiral, said gaps being inserted within both spirals.

3. The reamer according to claim 1, wherein each gap has a cylindrical shape.

4. The reamer according to claim 1, wherein at least some of the gaps have a frustoconical shape tapering inwardly in a proximal direction.

5. The reamer according to claim 1, wherein the cross section of the spiral coinciding with the gaps in the blade is round, oval, or of a different shape.

6. The reamer according to claim 1,
   wherein, after starting from a diameter of 0.25 mm and moving in a proximal direction along the blade, there is a first gap having a distal end with a diameter of 0.49 mm, beyond which the spiral starts again with a diameter of 0.49 mm;

wherein a second gap has a distal end coinciding with a spiral diameter of 0.73 mm, and the spiral starts again with a diameter of 0.65 mm;

wherein a third gap has a distal end coinciding with a spiral diameter of 0.89 mm and, beyond the gap, the spiral starts again with a diameter of 0.73 mm; and wherein a fourth gap has a distal end coinciding with a spiral diameter of 1.05 mm and the spiral starts again with a diameter of 0.97 mm.

7. A set of instruments with any series of diameters and taper angles, wherein each instrument includes a plurality of gaps in a pitch of a blade according to claim 1.

* * * * *